United States Patent [19]

Barber

[11] 4,367,731

[45] Jan. 11, 1983

[54] LOWER BODY SUPPORTING MECHANISM FOR A TILTABLE BODY EXERCISER

[76] Inventor: S. Morgan Barber, 138 N. Hwy. 95, Yerington, Nev. 89447

[21] Appl. No.: 251,484

[22] Filed: Apr. 6, 1981

[51] Int. Cl.[3] .................... A61F 5/00

[52] U.S. Cl. .................... 128/71; 272/145

[58] Field of Search .................... 128/24 R, 28, 68, 71, 128/70, 33, 73, 74, 75, 78, 80; 272/144, 145

[56] References Cited

U.S. PATENT DOCUMENTS

| | | | |
|---|---|---|---|
| 3,152,802 | 10/1964 | Heisler et al. | 128/71 |
| 3,286,708 | 11/1966 | Gartner | 128/33 |
| 3,568,669 | 3/1971 | Stites | 128/24 R |
| 4,114,613 | 9/1978 | Kuhn | 128/71 |
| 4,230,098 | 10/1980 | Uematus | 128/71 |
| 4,232,662 | 11/1980 | Barber | 128/71 |

*Primary Examiner*—Richard C. Pinkham
*Assistant Examiner*—T. Brown
*Attorney, Agent, or Firm*—B. F. Spencer

[57] ABSTRACT

A lower body supporting structure is disclosed for slidable adjustment along the lower end portion of an elongated central frame member of a tiltable body exerciser, the exerciser including an upper body supporting portion secured to the upper end of the central frame member. The lower body supporting structure includes an inverted U-shaped carriage member mounted upon and slidable along a substantially square central frame member. A step or foot rest laterally attached to the lower end of the carriage member is adapted to extend under each foot. A pair of laterally-extending ankle-area embracing members are adjustably attached to the carriage member. A manually releasable locking means, pivotally mounted to the lower end of the carriage member about the axis of the foot rest, includes a locking pin for insertion into and removal from a selected aperture within the central frame member. Release of the locking pin by raising the locking means permits both adjustment of the ankle-area embracing means and movement of the carriage member. A foot instep embracing means attached to a lever arm is adapted for engagement with the carriage member in interlocking fashion with the manually releasable locking means. Insertion of the lower end of the lever arm within the interlocking mechanism secures the lever arm, prevents movement of the locking pin, and secures the ankle-area embracing means. The upper end of the lever arm is releasably attached to the central frame member.

13 Claims, 5 Drawing Figures

LOWER BODY SUPPORTING MECHANISM FOR A TILTABLE BODY EXERCISER

BACKGROUND OF THE INVENTION

The present invention relates to therapeutic devices for treating and exercising the human body, and, in particular, to improvements in the lower body supporting mechanism of such devices. An example of one such device is disclosed in my U.S. Pat. No. 4,232,662, which disclosures are incorporated herein by reference.

The therapeutic device consists of a body supporting structure pivotally mounted upon a sturdy A-frame, the body supporting structure including an upper body supporting portion, a lower body supporting portion and a central elongated frame member interconnecting the upper and lower portions.

To achieve horizontal, inclined, or inverted positions of the body of a patient upon the exerciser requires the positioning of the center of gravity of the patient relative to the pivot axis of the exerciser. This positioning of the patient may be achieved in a number of ways, examples of which are disclosed in U.S. Pat. Nos. 3,152,802; 3,286,708; and 3,568,669, as well as in my aforesaid U.S. Pat. No. 4,232,662.

The balance of the patient upon the exerciser relative to the pivot axis may be controlled by slidably adjusting and locking the lower body supporting portion along the lower end portion of the central frame member. U.S. Pat. No. 4,114,613 discloses one type of slidable foot supporting device. When it is desired to place the body of the patient in an inclined or inverted position, it is of considerable importance that the patient be held in a safe, secure and comfortable manner. It is also preferable that adjustments of the center of gravity of the patient upon the exerciser be carried out in a controlled and gradual manner.

It is also highly desirable that the adjustment of body position be accomplished by the patient without outside assistance and in an easy and safe manner. Accordingly, the adjustments needed to slidably position and securely lock the lower body supporting mechanism should be within easy reach of the hands of the patient. Moreover, such adjustments should be made with comparative ease and without the necessity of completely dismounting from the exerciser. The locking mechanism for securing the lower body supporting portion to the central frame member and securing the patient to the lower body supporting mechanism must assure confidence in the patient that he or she may be safely suspended in an inverted position. The securing mechanism should, therefore, be interlocking, and the weight of the patient should be employed in such manner as to reinforce the security of the locking means.

Accordingly, the principal object of the present invention is to provide an improved lower body embracing mechanism for supporting the human body in an inverted position upon a tiltable body exerciser.

An additional object is to provide an adjustable lower body supporting mechanism that is readily positionable along and securely locked to a central supporting frame member.

Yet another object is to provide a lower body supporting mechanism which readily adjusts the balance of a patient with respect to the pivot axis of a tiltable body exerciser to achieve an inclined as well as an inverted body position.

Another object is to provide an adjustable lower body supporting mechanism which may readily accommodate a variety of different sizes and shapes of the human body.

A further object is to provide an improved manually releasable adjusting and locking means for the lower body supporting mechanism that is within easy reach of the hands of the patient.

The above objects of and the brief introduction to the present invention will be more fully understood, and further objects and advantages will become apparent, from a study of the following detailed description in connection with the drawings.

DESCRIPTION OF THE INVENTION

Figure 1:
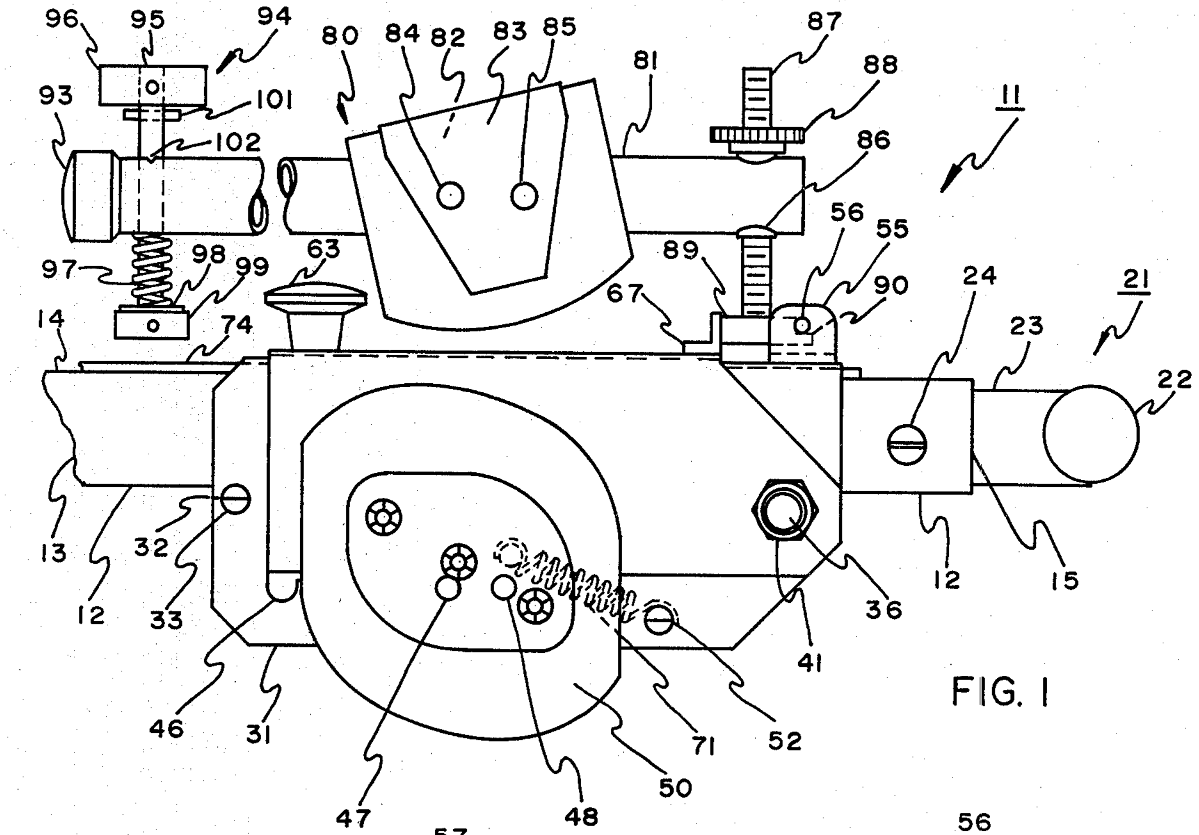
FIG. 1 is a side view of the improved lower body supporting mechanism of the invention.

Referring to FIG. 1, the lower body supporting mechanism 11 of the invention is mounted upon and is slidable along a substantially square, hollow elongated central frame member 12. The upper or left-hand end 13 of frame member 12 extends to join the upper body supporting portion of the tiltable body exerciser, as disclosed in my U.S. Pat. No. 4,232,662. The upper or top face of central frame member 12 includes a longitudinal slot extending the full length of central frame member 12.

Figure 4:
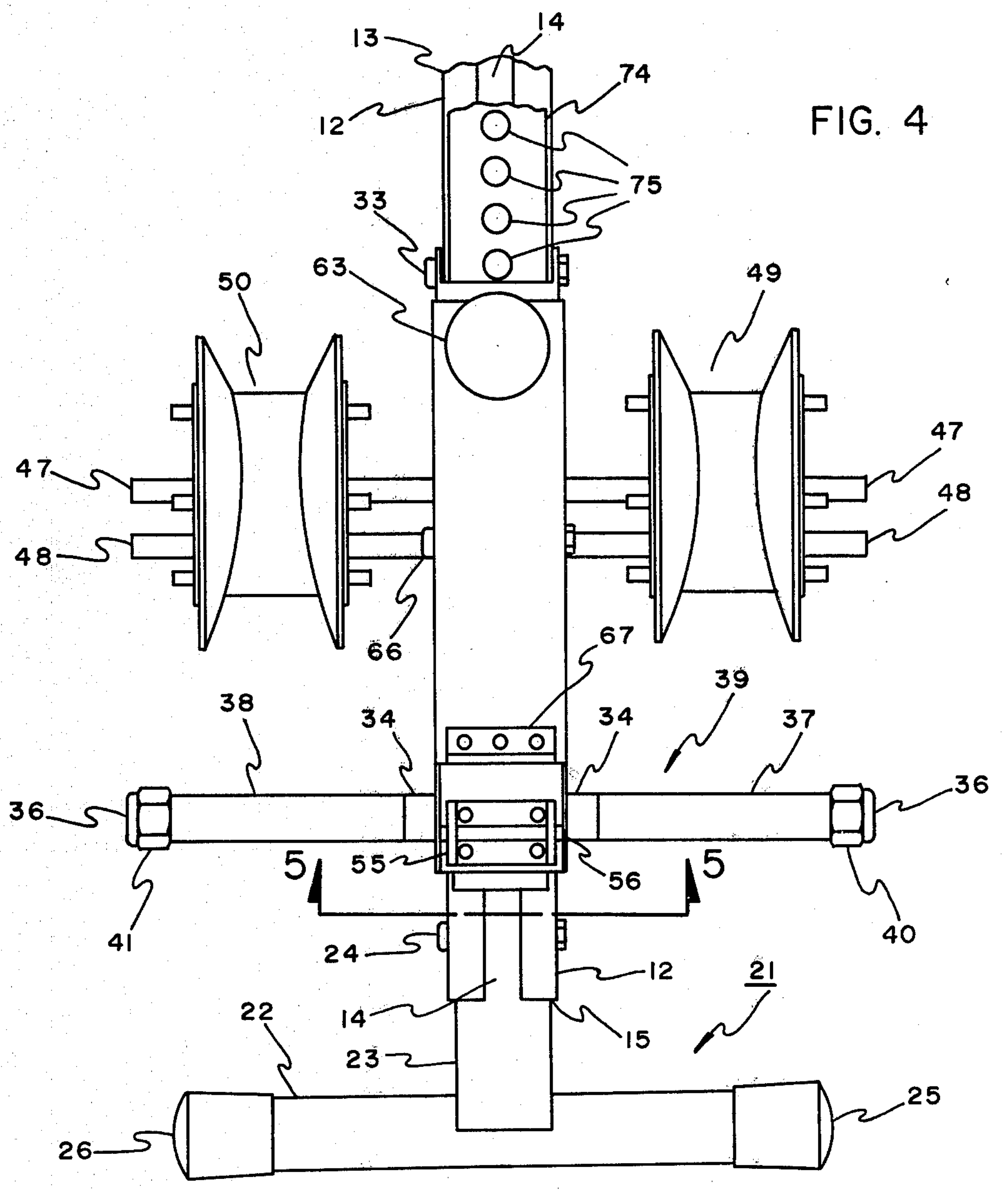
FIG. 4 is a top view of the ankle-area embracing members and step means of the supporting mechanism of FIG. 1.

The lower end 15 of central frame member 12 receives and supports floor rest 21. Floor rest 21 includes a cylindrical tube 22 extending laterally from each side of a square support channel 23 which telescopes within the open end section 15 of hollow frame member 12. The support channel 23 is secured to central frame member 12 by bolt 24. Each end of cylindrical tube 22 is capped with a plastic or rubber tip 25, 26 as illustrated in FIG. 4.

An inverted U-shaped carriage member 31 straddles central frame member 12 for sliding movement therealong. The left end of carriage member 31 is retained upon frame member 12 by a hollow sleeve member 32 positioned just below the bottom edge of member 12. Sleeve member 32 extends between the inside walls of carriage 31 and is retained by bolt 33. Sleeve member 32 serves to maintain proper spacing between the sides of carriage member 31 to assure easy sliding of the carriage upon frame member 12.

The right end of carriage member 31 is retained upon frame member 12 by a second and larger hollow sleeve member 34 positioned just below the bottom edge of member 12. Sleeve member 34 is pressed through hole 35 within each of the side walls of carriage member 31 and extends laterally from the side walls, as seen in FIG. 4. A large shaft 36, threaded at each end, passes through the center of sleeve member 34. Mounted upon shaft 36 are left and right cylindrical tube members 37,38 forming a step or foot rest 39, as seen in FIG. 4. The left and right tube members 37 and 38 of foot rest 39 are retained in abutment adjacent the ends of hollow sleeve 34 by locking nuts 40 and 41.

Sufficient clearance exists between the upper surfaces of hollow sleeves 32 and 34 and the bottom or lower surface of central frame member 12 to assure easy sliding of carriage member 31 upon frame member 12.

Figure 2:
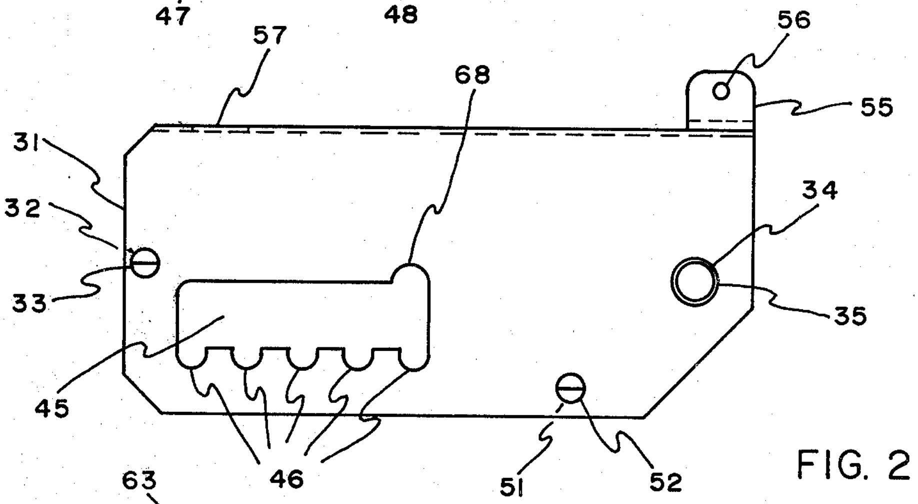
FIG. 2 is a side view of the carriage member of the supporting mechanism of FIG. 1.

The inverted U-shaped carriage member 31 is provided with a pair of identical cutouts 45, one through each side wall, as illustrated in FIG. 2. Each cutout 45 consists of a series of five spaced-apart, semicircular notches 46 located along the lower edge. The spaced-apart, semicircular notches 46 are employed in pairs to receive and support the center section of two rigid rod members 47 and 48. Rod members 47 and 48 extend through carriage member 31 and support left and right ankle-area embracing pads 49 and 50, as illustrated in FIG. 4. The center portions of rod members 47 and 48 are secured to each other by a clamping bracket (not shown) located between the side walls of carriage member 31. Rod members 47 and 48, with their corresponding ankle-area embracing pads 49 and 50, are substantially identical to those disclosed in my aforesaid U.S. Pat. No. 4,232,662.

The ankle-area embracing structure is adjustably positionable within adjacent pairs of notches 46 as may be required to achieve a comfortable fit with the ankles of the patient. Additionally, each of the ankle-area embracing pads 49 and 50 may be laterally positioned or slid along rod members 47 and 48 to vary the spacing between them in order to achieve a desired fit with the ankles of the patient.

The ankle-area embracing pads 49 and 50 are not symmetrically mounted upon rod members 47 and 48, as may be seen from FIG. 1. Instead, rod members 47 and 48 are slidably attached just above the geometric center of the pads. This feature allows the pads to be adjusted toward or away from the ankle area of the patient by simply rotating the ankle-area embracing assembly 180 degrees.

An additional hollow sleeve member 51 is positioned between the side walls of carriage member 31 near the lower edge to maintain the spacing between the side walls and to support one end of a coil spring, as will be described hereinafter. Sleeve 51 is retained in position by bolt 52.

A U-shaped holding bracket 55, having a horizontal pin 56, is securely attached to the top right-hand end of slidable carriage member 31. Bracket 55 and pin 56 serve as a pivot and anchor for one end of a removable lever arm, as will be described hereinafter.

The top left-hand end of carriage member 31 is provided with a circular hole 57 for cooperation with manually releasable locking means 60.

Figure 3:
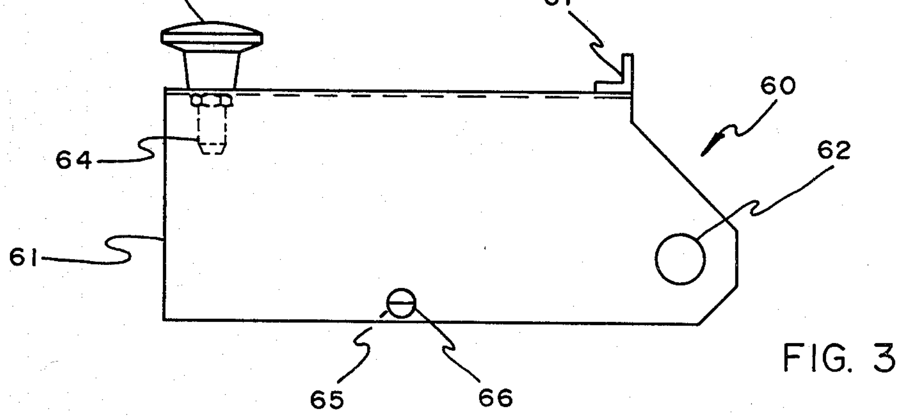
FIG. 3 is a side view of the manually releasable locking structure of the supporting mechanism of FIG. 1.

The manually releasable locking means 60 consists of a second inverted U-shaped member 61 straddling carriage member 31 and pivotally attached, at its lower or right-hand end, about hollow sleeve member 34 of foot rest 39. The lower right-hand end portion of U-shaped member 61 is provided with a pair of circular holes 62, one in each side wall, as shown in FIG. 3. The diameter of hole 62 is slightly larger than the outer diameter of sleeve member 34. Sleeve member 34 passes through holes 62 and serve as a bushing about which U-shaped member 61 may be pivoted.

The upper left-hand end of member 61 is provided with a round knob 63, extending above the top surface, and a locking pin 64, projecting downward between the side walls. Locking pin 64 is aligned to extend through the center of circular hole 57 in carriage member 31, as seen in FIG. 1.

A hollow sleeve member 65, extending between the inside walls of member 61, is secured by bolt 66. Sleeve member 65 maintains proper spacing between the inside walls of member 61 to assure clearance with the outside walls of carriage member 31, thereby enabling member 61 to pivot freely about sleeve 34 of foot rest 39. With member 61 of the manually releasable locking mechanism 60 installed upon carriage member 31, as shown in FIGS. 1, 4 and 5, hollow sleeve member 65 passes through the right-hand end of cutouts 45.

An L-shaped supporting bracket 67 is securely attached to the top right-hand end of member 61 for forming an anchor for the instep supporting lever arm, as will be described hereinafter.

The amount of travel of inverted U-shaped member 61 about the pivot axis of foot rest 39 is limited by the presence of sleeve member 65 extending through cutouts 45. Accordingly, knob 63 and locking pin 64, attached to member 61, can be raised upward by an amount determined by the travel of sleeve member 65 as it reaches a semicircular stop 68, formed as a part of the upper right-hand corner of cutout 45.

Figure 5:
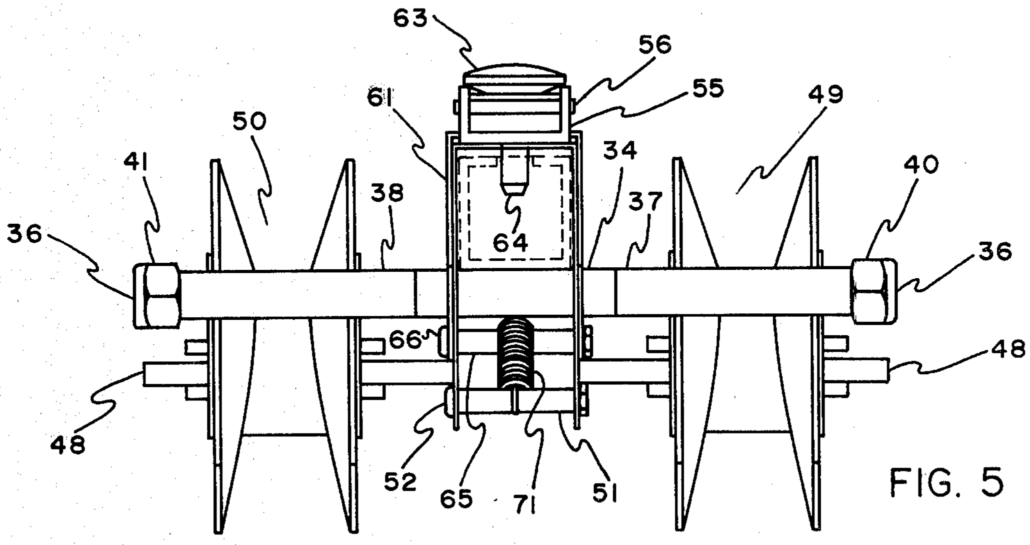
FIG. 5 is an end view of the structure of FIG. 4 taken along section 5—5.

The inverted U-shaped member 61 of manually releasable locking means 60 is normally maintained in a down or locked position by coil spring 71, as shown in FIGS. 1, 4 and 5. Coil spring 71 is located between the inside walls of carrage means 31, as shown in FIG. 5. The upper end of coil spring 71 is secured within a circular groove or undercut situated in the center of hollow sleeve member 65. The lower end of coil spring 71 is secured about a similar groove situated in the center of hollow sleeve member 51.

In the down or locked position, the lower or bottom edges of the two sides to member 61 bear upon the top surface of the two rigid rod members 47 and 48, thereby retaining them within their mating semicircular notches 46, as illustrated in FIGS. 1, 4 and 5.

The top face of central frame member 12 is provided with a securely attached, longitudinally extending, flat cover plate 74 overlying longitudinal slot 14, as illustrated in FIGS. 1 and 4. A series of uniformly spaced-apart holes 75 are distributed along the length of cover plate 74, each hole being situated over longitudinal slot 14. Each of the spaced-apart holes 75 is dimensioned to receive and pass locking pin 64 of the manually releasable locking mechanism 60.

The lower body supporting mechanism 11, which includes carriage member 31, foot rest 39, ankle-area embracing members 49 and 50 and manually-releasable locking means 60, is slidably positionable along the central frame member 12 when locking pin 64 is removed from hole 75 upon raising the pivoted inverted U-shaped member 61 by means of round knob 63. Removal of locking pin 64 allows the lower body supporting mechanism to be readily adjusted to any desired position along central frame member 12. With knob 63 in the raised position, the ankle-area embracing pads 49 and 50, supported on rod members 47 and 48, may be relocated, if desired, in different pairs of mating semicircular notches 46. Release of knob 63 allows coil spring 71 to return locking pin 64 into an appropriate hole 75, thereby locking carriage member 31 into position and securing the ankle-area embracing assembly.

The lower body supporting mechanism of the invention is provided with a foot instep embracing and supporting mechanism 80 similar, in part, to the foot instep embracing and supporting mechanism of my aforesaid U.S. Pat. No. 4,232,662. As illustrated in FIG. 1, instep mechanism 80 includes a hollow cylindrical lever arm 81 supporting left and right laterally extending foot instep pads 82, 83, each mounted upon a pair of rigid rods 84, 85.

The lower or right-hand end of lever arm 81 is provided with a hollow reenforcing tube member 86 extending diametrically through and securely attached to lever arm 81 for receiving threaded shaft 87. The upper end of threaded shaft 87 supports a threaded, knurled adjusting nut 88. The lower or bottom end of shaft 87 rigidly supports an attachment fitting 89 in the form of a rectangular block having a stepped portion 90. Attachment fitting 89 is adapted for insertion into U-shaped holding bracket 55 with stepped portion 90 extending underneath horizontal pin 56. The left-hand end of the block of attachment fitting 89 bears against the vertical face of L-shaped supporting bracket 67.

The upper or left-hand end of lever arm 81 is capped with a rubber or plastic tip 93. A spring-loaded fastener 94, shown in the disengaged position for ease of illustration, is attached to the upper end portion of lever arm 81, as shown. Fastener 94 includes a shaft 95 extending perpendicularly through lever arm 81. A rectangular knob 96 is pinned to the upper end of shaft 95 above the surface of lever arm 81.

The lower end portion of shaft 95 supports coil spring 97, shown in a compressed position for purposes of illustration, and a flat disk washer 98 situated below the lower end of spring 97. A rectangular key 99 is securely attached to the lower end of shaft 95 below spring 97 and washer 98. The length of rectangular key 99 is less than the inside width between side walls of hollow central frame member 12, and the width of rectangular key 98 is less than the width of longitudinal slot 14 in the top face of central frame member 12. The outer diameter of flat washer 98 is somewhat larger than the width of slot 14.

The upper end of lever arm 81 may be fastened to central frame member 12 by aligning rectangular key 99 parallel to slot 14, as shown, forcing the end of lever arm 81 toward central frame member 12 until key 99 passes through slot 14, and then manually rotating rectangular knob 96 90 degrees to secure key 99 within hollow central frame member 12. In the fastened position, flat washer 98 bears firmly against the top face of central frame member 12 under the force of spring 97 acting against the lower surface of lever arm 81. Additionally, a small pin 101, mounted through shaft 95 just below rectangular knob 96, is brought into engagement with a pair of V-notches or detents 102 located in the top surface of lever arm 81 adjacent shaft 95. Coil spring 97 provides a force sufficient to hold pin 101 within V-notches 102 and against accidental movement to knob 96, thereby retaining lever arm 81 in its fastened position.

The upper end of lever arm 81 may be disengaged from central frame member 12 by manually rotating rectangular knob 96 and additional 90 degrees, thereby overcoming the force of spring 97 and forcing pin 101 out of V-notches 102. Key 99 may then be withdrawn from slot 14 and lever arm 81 removed.

The feet of a patient are supported and secured to the lower body supporting mechanism of the invention in a manner similar to that disclosed in my aforesaid patent. The arches of the left and right foot of the patient are positioned, respectively, upon the left and right tube members 37 and 38 forming step or foot rest 39, with ankle-area embracing pads 49 and 50 adjusted to comfortably embrace the left and right ankles of the patient just above the heels. The left and right instep pads 82 and 83 on lever arm 81 also are properly adjusted and positioned to embrace the instep area of the left and right foot, respectively. With the upper end of lever arm 81 properly fastened to central frame member 12, the knurled nut 88 may be advanced or retarded along threaded shaft 87 to assure a comfortable and secure fit.

The lower body supporting structure of the present invention provides a number of important features and advantages not disclosed in prior art devices. The attachment of the lower end of lever arm 81 within supporting brackets 55 and 67 on the top surfaces of inverted U-shaped members 31 and 61 provides not only a secure anchor for lever arm 81 but also an interlock between carriage member 31 and the manually releasable locking mechanism 60. The insertion of attachment fitting 89, with its stepped portion 90, within U-shaped supporting bracket 55 and against the vertical face of L-shaped bracket 67 prevents the release of manually releasable locking mechanism 60. The presence of attachment fitting 89 between the supporting brackets 55 and 67 produces a wedge-like effect which prevents pivoting of inverted U-shaped member 61 about the pivot axis of foot rest 39. This feature secures release mechanism 60 in its locked position, and locking pin 64 cannot be withdrawn from hole 75 in cover plate 74.

It is apparent that manually releasable locking mechanism 60 should be in its down and locked position, as shown in FIG. 1, so that attachment fitting 89 can be inserted into U-shaped supporting bracket 55 and under horizontal pin 56. If for any reason release locking mechanism 60 is not in its locked position, i.e., locking pin has not entered hole 75 in cover plate 74, then lever arm 81, with attachment fitting 89, cannot be inserted into position within supporting brackets 55 and 67. Under this condition it will be obvious to the patient that the feet cannot be secured to the lower body supporting mechanism of the invention until slidable carriage 31 has been properly positioned and locking pin 64 has properly passed into one of the holes in cover plate 74.

Similarly, if rod members 47 and 48, supporting ankle-area embracing pads 49 and 50, are not properly positioned within mating U-shaped notches 46, then locking mechanism 60 cannot be placed in its down and locked position. Under this condition, attachment fitting 89 cannot be inserted into position between supporting brackets 55 and 67. It is necessary, therefore, for the patient to correctly position the ankle-area embracing structure within mating notches 46 in order for locking mechanism 60 to lock, thereby enabling attachment fitting 89 to be inserted between supporting brackets 55 and 67.

Another important feature is achieved when it is desired to place the body of a patient in an inclined or inverted position with the head being lowered below a horizontal position. In this position, the weight of the patient, acting through the instep supporting pads 82, 83 on lever arm 81 and the attachment fitting 89, produces a downward force upon supporting bracket 67. Since supporting bracket 67 is attached to and forms an integral part of locking mechanism 60, this downward force creates a moment about the pivot axis of foot rest 39 which aids in maintaining release mechanism 60 in its locked position. In the inverted position, this downward force is substantial, thereby further assuring the security of the lower body supporting mechanism.

To achieve inverted body position, it is necessary to shift the center of gravity of the patient relative to the pivot axis of the A-frame of the tiltable body exerciser. Although this may be done to a limited degree by the patient, while in position on the exerciser, by shifting the position of the arms and hands along the chest and below the head, the center of gravity may not shift by an amount sufficient to accomplish the desired inverted body position. It then becomes necessary for the patient to dismount from the exerciser in order to reposition the lower body supporting mechanism 11.

To dismount, the patient must lean forward to cause the body supporting structure to return to an upright position, with floor rest 21 firmly resting upon the floor. The patient then releases the upper end of lever arm 81 by rotating spring-loaded fastener 94 and withdrawing key 99 from slot 14. Lever arm 81, with instep embracing pads 82 and 83, is removed from lower body supporting mechanism 11 by raising the upper end of lever arm 81 to releasably disengage attachment fitting 89 from supporting brackets 55 and 67.

After removal of the foot instep embracing assembly, the patient may step down upon the floor while straddling lower body supporting mechanism 11. With release knob 63 within easy reach of the hands of the patient, being attached to the upper top face of release mechanism 60, lock pin 64 may be withdrawn from hole 75 in cover plate 74 by raising knob 63. While knob 63 is in its raised position, lower body supporting mechanism 11 may be slidably positioned in an upward direction on central frame member 12 in steps corresponding to the spacing between adjacent holes 75 in cover plate 74.

After lowering knob 63, thereby relocking supporting mechanism 11, the patient mounts the exerciser securing his or her feet in position upon foot rest 39 and within anklearea embracing pads 49, 50 and attaches lever arm 81 in position upon the supporting mechanism 11. By leaning backward upon the upper body supporting platform of the exerciser, the position of the center of gravity of the patient with respect to the pivot axis of the exerciser may be tested to determine if the desired inverted body position has been achieved.

An additional feature of importance results from the use of a hollow, square central frame member 12 having an elongated slot 14 extending along its length. This frame member 12, which is formed by the extrusion process, provides an economical and efficient structure for slidably carrying lower body supporting mechanism 11, supporting cover plate 74 with its series of uniformly spaced-apart holes 75 aligned over slot 14, and providing a secure and effective means for receiving and holding rectangular key 99. The attachment of cover plate 74 upon the top face and over slot 14 of frame member 12 also serves to stiffen the frame member against torsional forces produced as the patient mounts the exerciser. Similarly, the cylindrical tube 22 of floor rest 21, along with square support channel 23 telescoping within the lower end 15, further strengthens frame member 12.

Since many changes may be made in the above-described apparatus and many different embodiments of this invention could be made without departing from the scope thereof, it is intended that all matter contained in the above description or shown in the accompanying drawings shall be interpreted as illustrative and not in a limiting sense.

What is claimed is:

1. In a therapeutic device for the human body in which a main frame pivotally mounts a body supporting structure for longitudinal tilting movements, said body supporting structure having an elongated central frame member, an upper body supporting portion adapted for secure attachment to the upper end portion of said elongated central frame member, and a lower body supporting portion mounted upon and slidable along the lower end portion of said elongated central frame member, the improvement wherein said lower body supporting portion comprises:

(a) a carriage member mounted upon and slidable along the lower end portion of said elongated central frame member, said carriage member having upper and lower end portions;

(b) step means attached to the lower end portion of said carriage member, said step means being adapted to extend under each foot to form a support limiting endwise movement of the body in a downward direction when the body supporting structure is tilted so as to elevate the head of a body thereon above a horizontal position;

(c) a pair of ankle-area embracing members adapted for attachment to said carriage member intermediate its upper and lower end portions, said ankle-area embracing members extending laterally from each side of said carriage member; and (d) manually releasable locking means pivotally mounted with respect to the lower end portion of said carriage member, said manually releasable locking means including a knob with locking pin located adjacent the upper end portion of said carriage member, said locking pin being adapted for insertion into and removal from a selected one of a number of spaced-apart holes located within the lower end portion of said elongated central frame member, said locking pin preventing sliding movement of said carriage member along said elongated central frame member when inserted into a selected one of the holes within said elongated central frame member.

2. The therapeutic device as defined by claim 1 further comprisimg spring means intercoupled between said slidable carriage member and said manually releasable locking means for maintaining said slidable carriage member in a normally locked position relative to said elongated central frame member.

3. The therapeutic device as defined by claim 1 wherein said carriage member mounted upon and slidable along the lower end portion of said elongated central frame member is a first inverted U-shaped portion straddling said elongated central frame member, the sides of said first inverted U-shaped portion projecting downward and extending below the bottom surface of said elongated central frame member.

4. The therapeutic device as defined by claim 3, wherein said step means attached to the lower end portion of said carriage member is attached to the sides of said inverted U-shaped portion at a position beneath the bottom surface of said elongated central frame member.

5. The therapeutic device as defined by claim 4 wherein said manually releasable locking means pivotally mounted with respect to the lower end portion of said carriage member includes a second inverted U-shaped portion straddling said first inverted U-shaped portion, and wherein said second inverted U-shaped portion is pivotally mounted near its lower end with respect to said step means.

6. The therapeutic device as defined by claim 5 wherein said step means includes a rod member passing through the sides of said first inverted U-shaped portion and below the bottom surface of said elongated central frame member, said rod member projecting laterally from each of the sides of said first inverted U-shaped portion forming said carriage member.

7. The therapeutic device as defined by claim 6 wherein said rod member passing through the sides of said first inverted U-shaped portion also passes through the side walls of said second inverted U-shaped portion, and wherein said second inverted U-shaped portion is pivotally mounted near its lower end about the axis of said rod member.

8. The therapeutic device as defined by claim 5 wherein said knob with locking pin located adjacent the upper end portion of said carriage member is attached to the top surface of said second inverted U-shaped portion near its upper end, said locking pin extending downward between the side walls of said second inverted U-shaped portion.

9. The therapeutic device as defined by claim 1 further comprising attachment means secured to the lower end portion of said carriage member, said attachment means being adapted for securing one end of a removable lever arm.

10. The therapeutic device as defined by claim 9 wherein said carriage member includes an inverted U-shaped portion straddling said elongated central frame member and wherein said attachment means is secured to the top surface of said inverted U-shaped portion.

11. The therapeutic device as defined by claim 5 further comprising bracket means secured to the top surface of said second inverted U-shaped portion near its lower end, said bracket means being adapted for supporting one end of a removable lever arm.

12. In a therapeutic device for the human body in which a main frame pivotally mounts a body supporting structure for longitudinal tilting movements, said body supporting structure having an elongated central frame member, an upper body supporting portion adapted for secure attachment to the upper end portion of said elongated central frame member, and a lower body supporting carriage portion mounted upon and slidable along the lower end portion of said elongated central frame member, said lower body supporting carriage portion including locking means for securing said carriage portion to the lower end portion of said elongated central frame member, the improvement wherein said elongated central frame member comprises:

(a) a substantially square, hollow channel member having upper and lower end portions and a substantially flat upper wall portion;
(b) a longitudinal slot centrally situated within the flat upper wall portion of said square, hollow channel member, said longitudinal slot extending along the length of said channel member;
(c) a rectangular plate member securely attached to the flat upper wall portion of the lower end portion of said square, hollow channel member; and
(d) a series of spaced-apart holes extending through said rectangular plate member, said spaced-apart holes being positioned over said longitudinal slot, the lower body supporting carriage portion being slidable along the lower end portion of said square, hollow channel member and over said rectangular plate member, one of said spaced-apart holes in said plate member being adapted for engagement with the locking means of the lower body supporting carriage portion for securely locking the carriage portion to the lower end portion of said square, hollow channel member.

13. The therapeutic device as defined by claim 12 further comprisimg floor rest means, said floor rest means including a support channel having one end attached to the lower end portion of said square, hollow channel member and including a laterally extending cylindrical member attached to the other end of said square support channel, said floor rest serving to strengthen said square, hollow channel member against torsional movement.

* * * * *